(12) United States Patent
Hauptmann et al.

(10) Patent No.: US 7,890,269 B2
(45) Date of Patent: Feb. 15, 2011

(54) METHOD AND DEVICE FOR ACOUSTIC MEASUREMENT OF THE SPECIFIC DENSITY OF A GASEOUS OR LIQUID MEDIUM

(75) Inventors: Peter Hauptmann, Hermsdorf (DE); Alf Püttmer, Karlsruhe (DE); Robert Schäfer, Magdeburg (DE)

(73) Assignee: Siemens Aktiengesellschaft, Munich (DE)

( * ) Notice: Subject to any disclaimer, the term of this patent is extended or adjusted under 35 U.S.C. 154(b) by 128 days.

(21) Appl. No.: 11/921,259

(22) PCT Filed: Jun. 2, 2006

(86) PCT No.: PCT/EP2006/062885

§ 371 (c)(1),
(2), (4) Date: Dec. 19, 2008

(87) PCT Pub. No.: WO2006/128913

PCT Pub. Date: Dec. 7, 2006

(65) Prior Publication Data

US 2009/0093977 A1   Apr. 9, 2009

(30) Foreign Application Priority Data

Jun. 3, 2005 (DE) .................. 10 2005 025 671

(51) Int. Cl.
*G01N 31/00* (2006.01)
(52) U.S. Cl. ........................................... 702/23
(58) Field of Classification Search ............. 702/23; 367/35, 7; 340/388.1
See application file for complete search history.

(56) References Cited

U.S. PATENT DOCUMENTS

| | | | | |
|---|---|---|---|---|
| 5,339,282 | A  * | 8/1994 | Kuhn et al. | 367/7 |
| 5,671,136 | A | 9/1997 | Willhoit, Jr. | |
| 6,208,237 | B1 * | 3/2001 | Saiki et al. | 340/388.1 |
| 6,209,387 | B1 | 4/2001 | Savidge | |
| 6,538,958 | B1 * | 3/2003 | Blankinship et al. | 367/35 |

FOREIGN PATENT DOCUMENTS

DE    196 11 233 A1    9/1997
EP    0 797 105 A2    9/1997

OTHER PUBLICATIONS

Puttmer et al., "Ultraschallsensoren für die Prozesstechnik", Automatisierungstechnische Praxis, 2004, pp. 51-59, vol. 46, Issue 1.

* cited by examiner

*Primary Examiner*—Tung S. Lau
*Assistant Examiner*—Xiuquin Sun

(57) ABSTRACT

There is described a method and device for measurement of the specific density of a gaseous or liquid medium, whereby a pulsed acoustic signal is injected into the measured medium by means of a transmitting transducer, the signal is detected by a receiver transducer, after passing over a measured path, whereupon the acoustic impedance Z is automatically determined in an analytical device by comparison of a curve for the currently measured received signal with reference curves, predetermined for various values of the acoustic impedances stored for each value of the acoustic impedance, whereby the propagation speed c of the acoustic signal in the medium is determined and the density p of the medium is calculated as the quotient from the acoustic impedance Z and the propagation speed c. The method is preferably of application to an ultrasound mass flow measurement device and hence has the advantage that no additional density sensor is required, nevertheless permitting a robust and precise measurement of density.

18 Claims, 2 Drawing Sheets

METHOD AND DEVICE FOR ACOUSTIC MEASUREMENT OF THE SPECIFIC DENSITY OF A GASEOUS OR LIQUID MEDIUM

CROSS REFERENCE TO RELATED APPLICATIONS

This application is the US National Stage of International Application No. PCT/EP2006/062885, filed Jun. 2, 2006 and claims the benefit thereof. The International Application claims the benefits of German application No. 10 2005 025 671.6 DE filed Jun. 3, 2005, both of the applications are incorporated by reference herein in their entirety.

FIELD OF INVENTION

The invention relates to a method and to a device for the measurement of the specific density of a gaseous or liquid medium, a pulsed acoustic signal being injected into the measured medium by a transmitting transducer, the signal being detected by a receiving transducer after passing through a measured path and the density of the medium being inferred with the aid of an analysis of the received signal.

BACKGROUND OF INVENTION

From the article "Ultraschallsensoren für die Prozesstechnik" by Alf Püttmer, Edmund Linzenkirchner and Peter Hauptmann, published in atp (Automatisierungstechnische Praxis), 46 (2004), issue 1, pages 51 to 59, various application principles are known for ultrasound sensors when measuring physical or chemical values, such as temperature, pressure, throughflow, concentration and density. The use of ultrasonic transducers has the advantage that the ultrasonic waves penetrate through a container or tube wall and into the medium to be examined and therefore allow non-invasive measurement of the various values. The ultrasonic waves are emitted and received after interacting with the medium to be examined. They then carry information about the parameters to be measured. Sound generation and sound reception in process applications are usually carried out using piezoelectric sound transducers. In addition to the sound transducers an activating and analytical device is also required with which signal generation in the transmitting transducer is initiated, the electrical output signal of the receiving transducer detected and a signal analysis carried out. In an ultrasonic flowmeter two sound transducers, which are alternately called a transmitting transducer and a receiving transducer, are arranged on a measuring tube so as to be axially spaced apart. The propagation time difference method utilizes the carrying effect of a sound pulse with the flow inside the tube. This results in different propagation times, both in and counter to the direction of flow, from which the flow speed is calculated. The method is used in liquids and gases. With knowledge of the density of the medium and the geometry of the measuring tube the mass flow can be determined using the measured flow speed. In the case of media with changeable densities, the current density of the medium also has to be determined therefore to calculate the mass flow. This can take place using a separate ultrasonic density sensor. In principle the density of the medium could be inferred using an amplitude measurement of the received signal. The sound absorption depends on various properties of the media however, such as density, viscosity, thermal conductivity, thermal capacity or thermal coefficient of expansion. Determining the density using an amplitude measurement is therefore subject to a high level of inaccuracy owing to the strong cross-sensitivities.

An ultrasonic flowmeter is known for example from DE 196 11 233 A1. In this case a transmitting transducer emits pulsed signals which reach the receiving transducer as a wave group that increases and decreases again over a plurality of oscillations.

SUMMARY OF INVENTION

An object underlying the invention is to provide a method and a device for measurement of the specific density of a gaseous or liquid medium which allows robust and accurate measurement of the density of the medium.

To achieve this object the method comprises the features of an independent claim. Advantageous developments are described in the dependent claims.

The invention has the advantage that not a single parameter, such as the amplitude, but rather a temporal sub-domain of the measured characteristic of the received signal is used for determining the density. More signal information is therefore available and the density information contained in the signal form can be extracted. In an ultrasonic flowmeter, which operates according to the propagation time difference principle, components that are present anyway can be used exclusively for metrological implementation of the method. An additional density sensor is not necessary. In addition to the propagation times of the ultrasonic signals, which are determined for flow measurement, only the signal form of the received ultrasonic wave train has to be analyzed. The mass flow can thus be calculated on the basis of the flow rate, the density and the known geometry of the measuring tube with minimal metrological expenditure.

The temporal sub-domain advantageously includes the currently measured characteristic, which for determining the density is compared with corresponding sub-domains of reference characteristics, a region with a marked increase and/or marked decay in a wave group of the received acoustic signal that increases and decreases again over a plurality of oscillations. In particular the regions of the signal characteristic in which an envelope of the wave group, which increases and decreases again over a plurality of oscillations, markedly increases or decreases, have proven to be particularly relevant in determining the density. Improved accuracy is therefore attained by analyzing these temporal sub-domains. Temporal regions of the characteristic which are located before the start of the increase and after the end of the decay are, by contrast, no longer significant and should not be taken into account therefore when determining the density. So the position of the wave group in the time slots of the measured characteristic and the reference characteristics, which are compared with each other during analysis, is at least approximately the same, the effects of variations in the propagation speed of the acoustic signal in the measured medium can be compensated by adapting the temporal position of the sub-domains. This measure is particularly meaningful if the comparison is carried out in the time domain. Starting from the temporal position of the maximum oscillation in the wave group, which has the highest amplitude, a constant time value can be subtracted for this purpose. This time value is preferably selected such that the transient phenomenon is detected with the region of a marked increase in the envelope. The length of the temporal domain is advantageously selected in such a way that the decay phenomenon is also at least partially acquired. The position of maximum oscillation with the highest amplitude is dependent on the propagation speed and therefore changeable. It must be determined with the aid of the respective characteristic. The starting time and the duration of the analyzed temporal sub-domain should be selected so as to be optimally uniform for the characteristics in relation to the respective position of the maximum.

To determine the temporal position of the wave group, and therefore the relative position of the temporal sub-domain examined for the analysis, the methods known from DE 196 11 233 mentioned in the introduction are suitable as an alternative.

If, as an alternative to analysis in the time domain, a comparison is carried out in the frequency domain, compensation of the variations in the propagation speed are of secondary importance. In this case care should be taken that the upper and lower limiting frequencies are selected so as to be uniform for the analysis of the characteristics in the frequency range.

The detected received signal can advantageously be filtered by a band-pass filter before further processing in the analysis device, the pass range of which filter substantially centrally includes the resonance frequency of the sound transducer. Disruptive influences, such as a working noise in a process-engineering plant, which is in the low-frequency range, or high-frequency noises, can be significantly reduced thereby. A digital filter is preferably used for this purpose.

A model for the dependency of the acoustic impedance on the characteristics of the received signal is described by the stored reference characteristics of the received signal with the respectively associated reference values of the acoustic impedance. In the simplest case a linear characteristic can be assumed in the model used; two sampling points are required to determine the characteristic. At least two reference values of the acoustic impedance are required for this. There is no model-determined upper limit for the number of sampling points. However, in principle the following applies: the accuracy is increased if the number of sampling points is chosen so as to be relatively high. For practical reasons the number of sampling points used should be restricted to a minimum with which the desired accuracy can be attained since the amount of computing and computing time are highly dependent on the number of sampling points used. Use of 5 to 10 sampling points has proven to be advantageous and therewith a comparison of the measured characteristic with 5 to 10 reference characteristics.

A sampling rate which is between three and six times the resonance frequency of the sound transducer is advantageously used in digital signal processing in the analysis unit. Spectroscopic investigations have shown that the spectral distribution of the information relevant to the density is concentrated in a comparatively narrow range around the resonance frequency. With an ultrasonic transducer with a resonance frequency of 2.2 MHz, of which the received signal is filtered by a band-pass filter with an upper limiting frequency of 3 MHz, a sampling rate of 10 million samples per second has proven to be completely adequate. The sampling rate must not be selected too high since the number of sampling values to be taken into account when determining the density depends on the sampling rate and the length of the temporal sub-domain which is taken into account in the comparison. It has been found that when using 50 to 100 sampling values there is already enough density information in the temporal sub-domain being examined. A much reduced time slot would mean a poorer result, while only a small amount of additional, relevant information can be obtained with a marked increase in the time slot.

Comparison of the measured characteristic with stored reference characteristics for determining the acoustic impedance can advantageously be carried out on the basis of a mathematical method of linear regression since this is a method that has been proven in practice. The method of partial least squares regression (PLSR) provides even greater accuracy with good extrapolation properties in this connection.

The new method for density measurement can be applied particularly advantageously in an ultrasonic flowmeter which operates according to the propagation time difference principle. In this case no additional sensors have to be provided for density measurement. Furthermore, no changes to the control circuit for the sound transducer are required. Only the sequential control and an analysis program in an analysis device based on a microcontroller have to be adapted to the new method.

BRIEF DESCRIPTION OF THE DRAWINGS

The invention and embodiments and advantages will be described in more detail hereinafter with reference to the drawings in which an exemplary embodiment of the invention is illustrated, and in which.

DETAILED DESCRIPTION OF INVENTION

Figure 1:
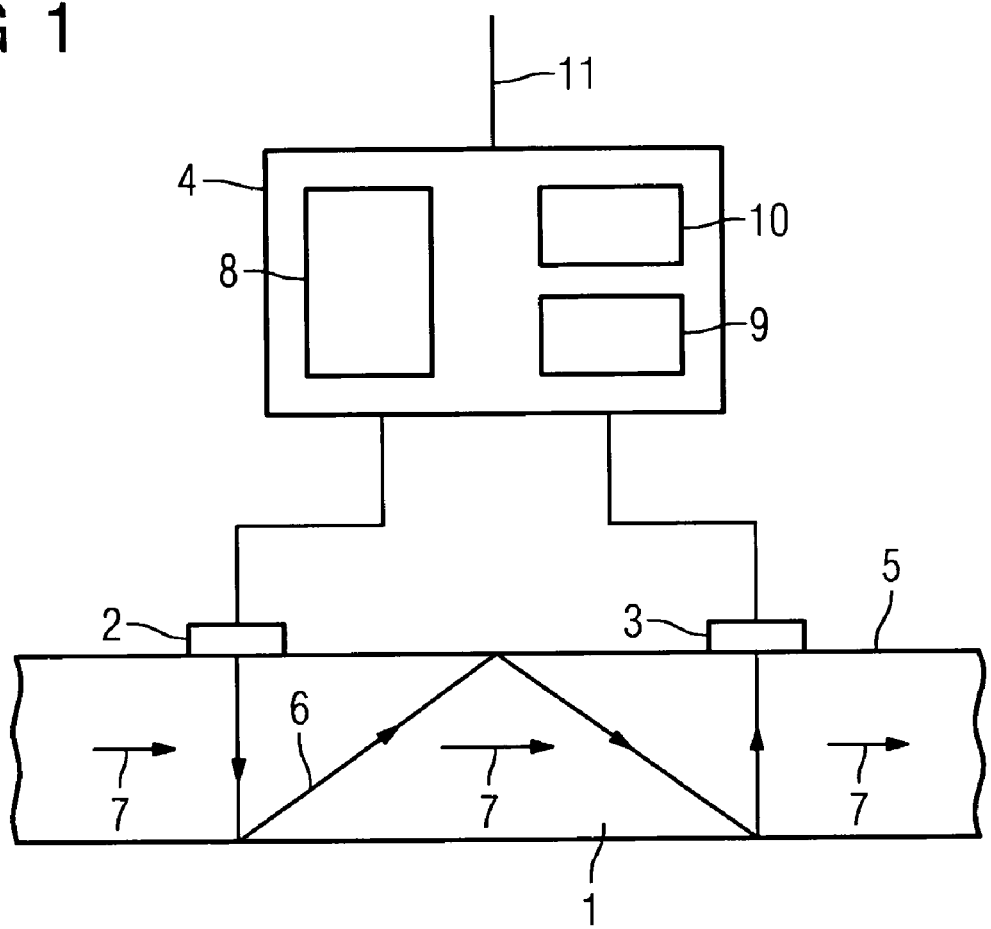
FIG. 1 shows a block diagram of a mass flowmeter by means of ultrasound.

According to FIG. 1 a device for measuring the density of a measured medium 1 includes a transmitting transducer 2, a receiving transducer 3 and an analysis device 4. The measured medium 1 flows through a measuring tube 5, on the wall of which the transmitting transducer 2 and receiving transducer 3 are arranged in such a way that they perpendicularly inject an acoustic signal 6 into the measured medium 1 and detect it as a received signal. The acoustic signal 6 runs downstream in a W-shaped manner through the measuring tube 5 in a flow direction 7 of the measured medium 1. For measuring the flow rate the two transducers 2 and 3 are alternately operated as transmitting and receiving transducers, so the flow rate can be determined in a known manner from the difference between the signal propagation times measured downstream and upstream. In principle a single transducer would also be sufficient solely for measuring the density if the acoustic signal were to be reflected back to it. However the device shown in FIG. 1 has the advantage that both the flow rate of the medium 1 and its density can be measured using the same transducers. An additional density sensor is not required therefore. The analysis device 4 is used to control the two transducers 2 and 3 and to analyze the detected received signals. For this purpose it includes a microcontroller 8 and a program memory 9 which includes a program capable of carrying out the measurement. Reference characteristics of the received signal are stored for the density measurement in a memory 10, with which characteristics a current characteristic of the received signal is compared for determining the density. The determined values of the flow rate of the measured medium 1, its density and the mass flow rate through the tube 5 are output via a line 11, which, for example, can be a field bus of an automation-technological system, to a higher-order memory-programmable controller. The controller uses these values as actual values for example to regulate the mass flow rate.

Figure 2:
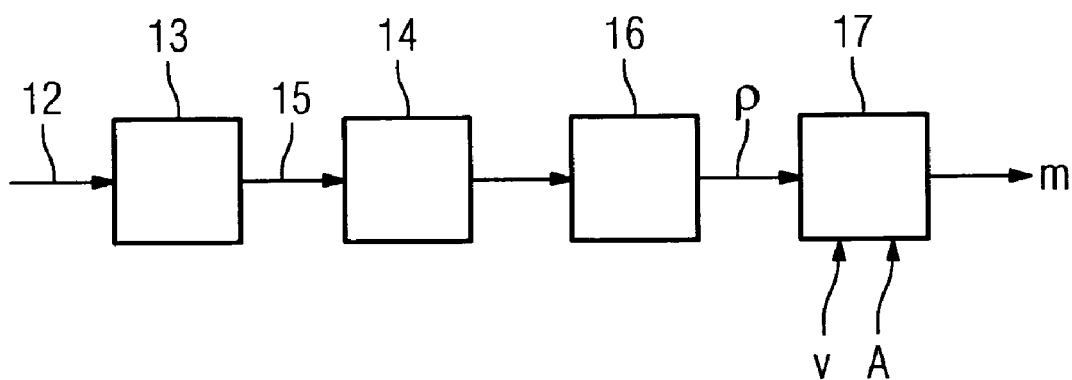
FIG. 2 shows a flow diagram of signal processing in an analysis device.

FIG. 2 shows the basic progression of signal processing for measuring the density of the medium and finally for determining the mass flow rate ṁ through the measuring tube 5 (FIG. 1). A received signal 12 is firstly freed from disruptive ambient noise in a digital band-pass filter 13, of which the lower limiting frequency is 1.5 MHz and the upper limiting frequency 3.0 MHz. A digital IIR (Infinite Impulse Response) or FIR (Finite Impulse Response) filter for example is suitable as the band-pass filter 13. In principle filtering can however also take place by transformation in the frequency range, elimination of undesirable frequency fractions and inverse transformation in the time domain since it is energy signals that are involved. The two limiting frequencies of the band-pass filter 13 are adapted to the resonance frequency of the sound transducers 2 and 3 (FIG. 1) in such a way that they substantially centrally include their resonance frequency of 2.2 MHz. During a subsequent temporal standardization 14 the start of the temporal sub-domain of the characteristic of the filtered received signal 15 is fixed, so changes in the propagation speed of the acoustic signal 6 (FIG. 1) are compensated. Only values of the filtered received signal 15 which lie within the temporal sub-domain are processed further in a comparison 16 to determine the density ρ. The comparison 16 takes place with corresponding reference characteristics of the received signal which are predetermined for various values of the acoustic impedance and stored so as to be associated with the respective values. These reference characteristics and values of the acoustic impedance can have been determined in a calibration process carried out in advance and stored. The comparison 16 supplies a value of the acoustic impedance Z which is equal to the product of the sound propagation speed c and the density ρ of the medium. The speed c can be determined from the distance between transmitter and receiver and the sound propagation time. The density ρ is calculated as the quotient from the acoustic impedance Z and the propagation speed c. The value of the density ρ, together with a flow rate v and a geometric cross-sectional area A of the measuring tube 5 (FIG. 1), enters into a calculation 17 in which the mass flow rate ṁ through the measuring tube is determined.

Figure 3:
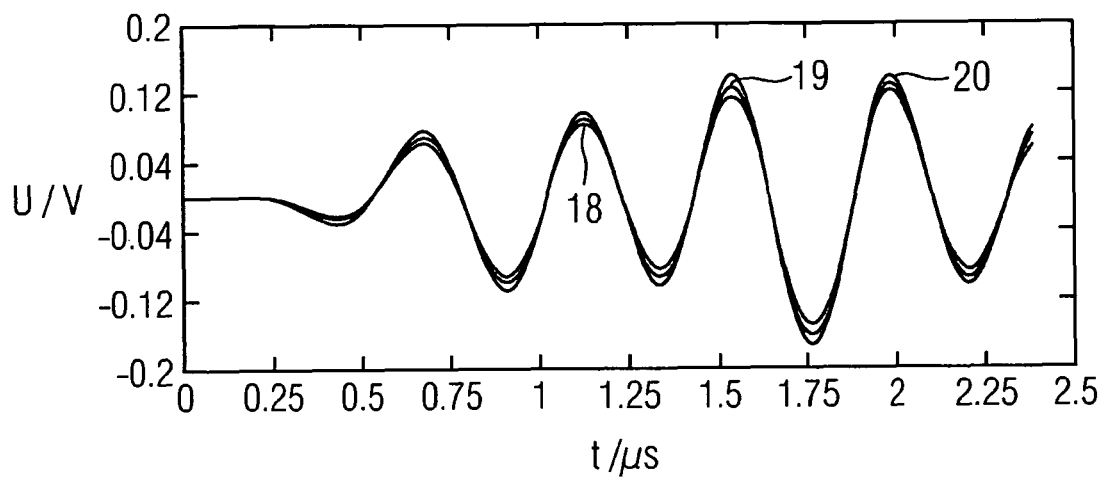
FIG. 3 shows stored reference characteristics of a received signal.

The characteristic of the acoustic received signal is also analyzed in addition to the propagation times of the ultrasonic signal in a mass flowmeter to determine the density of the measured medium in the described manner. The signal form for analysis is influenced inter alia by the density of the medium contained in the measuring tube. FIG. 3 shows three characteristics 18, 19 and 20 for various densities in a standardized temporal sub-domain. The time t in microseconds (μs) is plotted on the abscissa, the voltage U in volts (V) on the ordinate. Water mixed with sodium chloride was used as the measured medium. Various density values were adjusted by way of a different sodium chloride concentration: 998.01 kg/m³ for characteristic 18, 1077.03 kg/m³ for characteristic 19 and 1121.04 kg/m³ for characteristic 20. It is clear from the differences in the signal characteristics 18 . . . 20 that there is sufficient information provided to determine the density in further processing of the characteristics.

Figure 4:
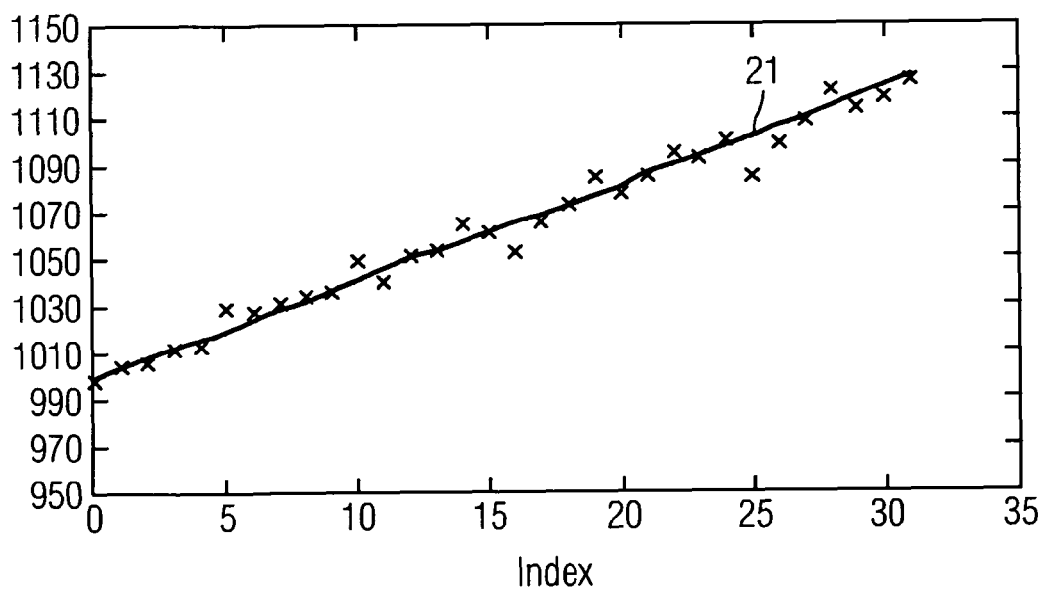
FIG. 4 shows a graph to illustrate the accuracy of density determination.

In FIG. 4 approximately 30 determined density values are respectively marked with a cross to illustrate the accuracy. The actual density of the measured medium, which was determined using a very accurate method, is shown as characteristic 21. The number of the respective measurement is plotted as an index on the abscissa, the density ρ in kg/m³ on the ordinate. It can be seen that the difference of the determined density from the actual value is comparatively low.

The density of the liquid medium is determined using received ultrasound signals of a given ultrasonic flowmeter with the aid of a numerical comparison of the signal forms of a finite number of reference pulses sampled in a time-discrete manner and reference values of the acoustic impedance that are clearly allocated thereto with the signal form of a sampled pulse. The method therefore uses the dependency of the signal form on the acoustic impedance. The numerical comparison is based on a linear regression model $$Z = X \cdot b \quad (1)$$

where z is a vector with various values of acoustic impedance, X is the matrix of the described variables (descriptor matrix) and b the coefficient vector of the model. b should be determined first of all in a calibration step. A vector with reference values of the acoustic impedance $Z_0$ and a clearly allocated descriptor matrix $X_0$ are required for this. The system of equations (1) according to b should be solved by standard linear algebra methods (for example Gaussian algorithm, Cramer's rule, Cholesky method, etc.)

$$b = X_0^{-1} Z_0 \quad (2)$$

An unknown acoustic impedance $Z_x$ that is to be determined involves a sampled pulse which results in a clearly determined descriptor matrix $X_x$. The unknown acoustic impedance can accordingly be determined using $$Z_x = X_x \cdot b \quad (3).$$

There are various methods of resolution for establishing a descriptor matrix X from the sampled pulses U. Formally the algorithm used should be called an operator f, so $$X = f\{U\} \quad (4).$$

Comparison on the basis of the mathematical method of linear regression will firstly be described in more detail below.

The method allocates the acoustic impedance of the respective medium contained in the measuring tube to the various signal forms. Knowledge of individual reference values of the acoustic impedance with the corresponding signal forms is required for this. There are $\underline{X}_i | i = 1, \ldots, n$ spectral vectors which as elements each contain $j = 1, \ldots, m$ sampled values of a received ultrasound signal. Element $x_{ij}$ therefore designates the j-th sampled value of the i-th received signal. Matrix $X = [x_{ij}]$ is designated the measured value matrix. The columns $k = 1, \ldots, n-1$ of X contain the signals sampled in the case of the known reference values $Z_k$. The column vector $\underline{Z}_{ref}$ contains $Z_k$ as elements. Column n of X contains the signal sampled in the case of the acoustic impedance $Z_n$ to be determined. The information about the acoustic impedance is extracted by means of a matrix decomposition. The decomposition rules known from linear algebra: singular value decomposition (SVD), QR decomposition, LU decomposition and primary component analysis (PCA), could be successfully used for the extraction.

Use of SVD is mentioned at this point by way of example. Using SVD the measured value matrix is decomposed into three matrices U, S and V, so $$X = USV^T$$

The product $S \cdot V^T$ is equal to a transposed weighted matrix $W^T$. The matrix W contains the extracted information for allocating a value of the acoustic impedance and can be split into a sub-matrix $W_{ref}$ and a row vector $\underline{V}_n^T$, where $W_{ref}$ includes the first n−1 lines of W and $\underline{V}_n^T$ is equal to the last line of W. Since each signal form can be allocated a value of the acoustic impedance there is a coefficient vector $\underline{M}$ which satisfies the equation $$\begin{pmatrix} Z_{ref} \\ Z_n \end{pmatrix} = \begin{pmatrix} W_{ref} \\ \underline{V}_n^T \end{pmatrix} \cdot M$$

It follows from this that the acoustic impedance to be determined can be calculated with the aid of $$Z_n = \underline{V}_n^T \cdot ((W_{ref}^T \cdot W_{ref})^{-1} \cdot W_{ref}^T \cdot Z_{ref})$$

The developed method can equally be employed by using alternative decomposition rules for extraction of the information about the acoustic impedance. In addition to singular value decomposition the following decomposition rules have been investigated and found to be suitable for the method:

1) QR decomposition

2) LU decomposition

3) PCA

All three rules use the measured value matrix X as the input and provide a weighted matrix W as the output. Forming the respective weighted matrix shall be briefly described hereinafter.

1) QR Decomposition

The QR algorithm known from linear algebra decomposes the measured value matrix X into an orthogonal matrix Q and an upper triangular matrix R, so $$X = Q \cdot R.$$

$W_{ref}$ is equal to the first n−1 columns of R. $\underline{V}_n$ is equal to the n-th column of R.

2) LU Decomposition

The LU algorithm known from linear algebra decomposes X into a lower triangular matrix L and an upper triangular matrix U, so $$X = L \cdot U$$

$W_{ref}$ is equal to the first n−1 columns of U. $\underline{V}_n$ is equal to the n-th column of U.

3) PCA

Primary component analysis known from linear algebra decomposes X into a charge matrix B and a factor matrix F, so $$X = B \cdot F$$

$W_{ref}$ is equal to the first n−1 columns of F. $\underline{V}_n$ is equal to the n-th column of F.

All other method steps are unaffected by the choice of decomposition rule.

A modified method will be described below which uses a partial least squares approach which is based on that of the described linear regression model. The name partial least squares regression (PLSR) is generally conventional in this context. Since PLSR is also very well suited to multiple regression and for preserving the generally conventional standard in the description, the value to be determined shall be characterised hereinafter by Y. This therefore means Y=Z for determining the acoustic impedance.

There are substantially three differences from the above-mentioned method. Firstly, the coefficient vector is calculated using the result from the PLSR algorithm and not separately by an explicit resolution of the system of equations. Secondly, the reference descriptor matrix and the reference vector of the acoustic impedance itself constitute the input variables for the PLSR algorithm and thirdly, the transformation used in the algorithm is applied not only to X but rather to the cross-covariance matrix $Y^T X$. Forming the cross-covariance matrix amounts to a filter effect which intensifies the connection between Y and X or suppresses the effect of other variables on Y. The high level of effectiveness and the superiority of PLSR inter alia result from this.

Various algorithms exist for PLSR, thus for example the NIPALS algorithm or the SIMPLS algorithm. PLSR has been a standard method in chemometry for a fairly long time whereas its application in ultrasonic measuring systems in the non-chemometric, acoustic sector of ultrasonic flow measuring is not known. For this reason there is no need to describe PLSR as a calculation rule in detail. Only the individual steps of the calculation rule in the application and corresponding input and output variables shall be cited.

Input variables for PLSR are the reference descriptor matrix $X_0$ and the reference values of the acoustic impedance $Y_0$. Output variables for PLSR are the factor matrix T, the weighting matrix W and the charge matrix Q, so equation (5) is satisfied $$PLSR\{X, Y, d\} = (T, W, Q) \longrightarrow \begin{cases} Y = T \cdot Q^T \\ T = X \cdot W \end{cases} \quad (5)$$

Where $b = W \cdot Q^T$ $$Y = X \cdot b \quad (6)$$

directly follows from (5) and this corresponds to the linear regression model of equation (1). The algorithm used, which is a modified NIPALS algorithm, will be described hereinafter. The number of PLS components to be formed ($X_i = X$, $Y_i = Y$) is assigned to the algorithm as the parameters X, Y and d. The number of iteration steps or the number of PLS components can be set by the parameter d. If d is equal to the number of eigenvalues of the cross-covariance matrix, the variance of Y in X is completely explained by the return values of the PLSR. A smoothing effect occurs for smaller values of parameter d. Smaller variances, for example those caused by noise, are not incorporated in the regression model. The parameter d is optimally selected if it is precisely the random variance (noise) that no longer enters the regression model. This should be determined by way of experiments in the development process for the measuring system and regression model used. The algorithm then operates iteratively in steps i=1, . . . , d, the following calculations being carried out in the i-th step:

1. Formation of the cross-covariance matrix $$(C_{YX})_i = Y_i^T X_i \quad (7.1)$$

2. Calculation of the dominant eigenvector of the cross-covariance matrix. The highest eigenvalue of the cross-covariance matrix is associated with this vector. It can be determined for example with the aid of SVD.

$$SVD[(C_{YX})_i] = (U_i, S_i, V_i) \rightarrow (C_{YX})_i = U_i S_i V_i^T \quad (7.2)$$

$$w_i = U_i^{(0)} \quad (7.3)$$

The vector $W_i$ should be designated the i-th weighting vector.

3. Calculation of the i-th factor vector by multiplication by the descriptor matrix $$t_i = X_i w_i \quad (7.4)$$

4. Calculation of the i-th associated charge vector for X $$p_i = \frac{X_i^T t_i}{t_i^T t_i} \quad (7.5)$$

5. Calculation of the i-th associated charge vector for Y $$q_i = \frac{Y_i^T t_i}{t_i^T t_i} \quad (7.6)$$

6. Calculation of the residues for X and Y $$E_i = X_i - t_i P_i^T \quad (7.7)$$

$$F_i = Y_i - t_i q_i^T \quad (7.8)$$

7. Write calculated vectors into the corresponding return matrices and calculate the new X and Y from the residues $$T(i) = t_i \to T = (t_1, t_2, \ldots, t_c) \quad (7.9)$$

$$W(i) = w_i \to W = (w_1, w_2, \ldots, w_c) \quad (7.10)$$

$$Q(i) = q_i \to Q = (q_1, q_2, \ldots, q_c) \quad (7.11)$$

$$X_{i+1} = E_i \quad (7.12)$$

$$Y_{i+1} = F_i \quad (7.13)$$

NIPALS and SIMPLS algorithms should also be mentioned here as possible alternative solutions.

The acoustic impedance is accordingly determined in two phases analogously to the methods already described.

The first phase is the training phase or calibration. In this connection the matrices T, Q and W are determined for a limited set of reference descriptors $X_0$ with corresponding reference values of the acoustic impedance $Y_0$ using PLSR and where $$b = W \cdot Q^T \quad (8)$$

calculates the regression coefficients. Here the reference descriptors are the discrete and band-limited spectra of the reference pulses stored as row vectors in $X_0$. Conventional IIR and FIR filters can be used as the filter. If analysis takes place in the spectral range the start of the sampling process tends not to be critical. The wave train should be largely included.

In the second phase the corresponding value of the acoustic impedance can be calculated according to equation (3) for any desired, sampled and filtered ultrasonic pulse or—in the case of analysis in the spectral range—for the discrete spectra thereof.

Application of the PLSR method to the same measured data, which also forms the basis of the described method of linear regression, exhibited the following results:

1. The PLSR-based method is more effective by comparison. In one experiment 8 of 33 values, i.e. every fourth value, of the acoustic impedance were incorporated as reference values for interpolation. Where d=7 all values of the acoustic impedance could be determined with a relative error of 0.4%. By comparison: using the linear regression method only one error of 0.75% was achieved.

2. The PLSR-based method allows an extrapolation. This could also be confirmed by experiments. The extrapolation was also carried out using 8 of 33 possible acoustic impedance values. This time the smallest eight values were successively used as sampling points, however. After calculation of the density these covered a range of 1000 kg·m$^{-3}$ to 1027 kg·m$^{-3}$. In other words, the majority of the measuring range up to 1150 kg·m$^{-3}$ was not represented by sampling points. Nevertheless, using the PLSR-based method the density values could be extrapolated with a relative error comparable to interpolation of 0.42%.

3. The used PLSR algorithm works comparatively quickly and provides results of acceptable accuracy in a relatively short time.

The invention claimed is:

1. A method for measurement of the specific density of a medium, comprising:
    injecting a pulsed acoustic signal into the measured medium by a transmitting transducer;
    detecting the signal by a receiving transducer after passing through a measured path;
    determining automatically the acoustic impedance Z of the medium in an analytical device by comparison of the characteristic for the currently measured received signal with reference characteristics predetermined for various values of the acoustic impedance and stored so as to be associated with the respective values of the acoustic impedance, wherein the comparison is made in at least one temporal sub-domain of the characteristics;
    determining the propagation speed of the acoustic signal in the medium; and
    calculating the density of the medium as a quotient from the acoustic impedance Z and the propagation speed,
    wherein the comparison is based on a linear regression, and
    wherein the signal is digitally processed in the analytical device using a sampling rate which is between three and six times the resonance frequency of the transducers.

2. The method as claimed in claim 1, wherein the medium is a gaseous medium.

3. The method as claimed in claim 1, wherein the medium is a liquid medium.

4. The method as claimed in claim 1, wherein the temporal sub-domain includes a region with a marked increase in a wave group of the received acoustic signal that increases and decreases again over a plurality of oscillations.

5. The method as claimed in claim 1, wherein the temporal sub-domain includes a region with a marked decay in a wave group of the received acoustic signal that increases and decreases again over a plurality of oscillations.

6. The method as claimed in claim 1, wherein the effects of variations in the propagation speed of the acoustic signal in the measured medium are compensated by adjusting the temporal position of the sub-domain.

7. The method as claimed in claim 1, wherein before further processing in the analytical device, the detected received signal is filtered by a band-pass filter, wherein a pass range of the band-pass filter essentially centrally includes the resonance frequency of the transducers.

8. The method as claimed in claim 1, wherein between 5 and 10 reference characteristics are used for the comparison.

9. The method as claimed in claim 1, wherein each stored reference characteristic is depicted by 50 to 100 sampled values.

10. The method as claimed in claim 1, wherein said method is applied in an ultrasonic flowmeter.

11. A device for a measurement of a specific density of a gaseous or liquid medium, comprising:
    a transmitting transducer to inject a pulsed acoustic signal into the measured medium;

a receiving transducer to detect an acoustic received signal after passing through a measured path in the measured medium; and an analytical device, wherein the acoustic impedance Z of the medium is automatically determined based on the design of the analytical device by comparison of the characteristic for the currently measured received signal with reference characteristics predetermined for various values of the acoustic impedance and stored so as to be associated with the respective value of the acoustic impedance, wherein the comparison is made in at least one temporal sub-domain of the characteristics, wherein the propagation speed c of the acoustic signal is determined in the medium and wherein the density $\rho$ of the mediums is calculated as the quotient from the acoustic impedance Z and the propagation speed c, wherein the comparison is based on a linear regression, or wherein the comparison is based on a partial least squares regression, and wherein the signal is digitally processed in the analytical device using sampling rate which is between three and six times the resonance frequency of the transducers.

12. The device as claimed in claim 11, wherein the transmitting transducer, the receiving transducer and the analytical device are components of an ultrasonic flowmeter.

13. A method for measurement of the specific density of a medium, comprising:

injecting a pulsed acoustic signal into the measured medium by a transmitting transducer;

detecting the signal by a receiving transducer after passing through a measured path;

determining automatically the acoustic impedance Z of the medium in an analytical device by comparison of the characteristic for the currently measured received signal with reference characteristics predetermined for various values of the acoustic impedance and stored so as to be associated with the respective values of the acoustic impedance, wherein the comparison is made in at least one temporal sub-domain of the characteristics;

determining the propagation speed of the acoustic signal in the medium; and calculating the density of the medium as a quotient from the acoustic impedance Z and the propagation speed, wherein the comparison is based on a partial least squares regression, and wherein the signal is digitally processed in the analytical device using a sampling rate which is between three and six times the resonance frequency of the transducers.

14. The method as claimed in claim 13, wherein said method is applied in an ultrasonic flowmeter.

15. The method as claimed in claim 13, wherein the temporal sub-domain includes a region with a marked increase in a wave group of the received acoustic signal that increases and decreases again over a plurality of oscillations.

16. The method as claimed in claim 13, wherein the temporal sub-domain includes a region with a marked decay in a wave group of the received acoustic signal that increases and decreases again over a plurality of oscillations.

17. The method as claimed in claim 13, wherein the effects of variations in the propagation speed of the acoustic signal in the measured medium are compensated by adjusting the temporal position of the sub-domain.

18. The method as claimed in claim 13, wherein before further processing in the analytical device, the detected received signal is filtered by a band-pass filter, wherein a pass range of the band-pass filter essentially centrally includes the resonance frequency of the transducers.

* * * * *